(12) United States Patent
Futatsuyama et al.

(10) Patent No.: US 10,905,338 B2
(45) Date of Patent: Feb. 2, 2021

(54) PULSE WAVE MEASURING DEVICE

(71) Applicant: DENSO CORPORATION, Kariya (JP)

(72) Inventors: Koki Futatsuyama, Kariya (JP); Mitsuyuki Kobayashi, Kariya (JP); Taiji Kawachi, Kariya (JP); Hiroshi Yamakita, Kariya (JP)

(73) Assignee: DENSO CORPORATION, Kariya (JP)

( * ) Notice: Subject to any disclaimer, the term of this patent is extended or adjusted under 35 U.S.C. 154(b) by 942 days.

(21) Appl. No.: 15/584,059

(22) Filed: May 2, 2017

(65) Prior Publication Data

US 2017/0332920 A1 Nov. 23, 2017

(30) Foreign Application Priority Data

May 19, 2016 (JP) ................................ 2016-100476

(51) Int. Cl.
*A61B 5/021* (2006.01)
*A61B 5/00* (2006.01)
*A61B 5/024* (2006.01)

(52) U.S. Cl.
CPC ........ *A61B 5/02108* (2013.01); *A61B 5/7203* (2013.01); *A61B 5/7225* (2013.01); *A61B 5/7278* (2013.01); *A61B 5/742* (2013.01); *A61B 5/024* (2013.01)

(58) Field of Classification Search
None
See application file for complete search history.

(56) References Cited

U.S. PATENT DOCUMENTS

2008/0242956 A1* 10/2008 Suzuki ................ A61B 5/4035
600/301
2012/0089039 A1* 4/2012 Felix ................... A61B 5/7203
600/523

FOREIGN PATENT DOCUMENTS

JP 3584140 B2 11/2004
JP 2014-212796 A 11/2014

* cited by examiner

*Primary Examiner* — Matthew Kremer
(74) *Attorney, Agent, or Firm* — Harness, Dickey & Pierce, P.L.C.

(57) ABSTRACT

A pulse wave measuring device checks whether amplitude of a pulse signal satisfies a gain changing condition and, when the gain changing condition is satisfied, changes a gain. The pulse wave measuring device includes an amplitude storing unit and a mode progressing unit. The amplitude storing unit stores plural gain changing conditions, to which a series of order are assigned, respectively. A mode progressing unit 15 changes the gain changing condition to the next-ordered gain changing condition upon determination that the mode progress condition is satisfied. The gain changing condition is satisfied in case that Y1 or more number of pieces of X1 amplitudes are larger than an upper limit value U1 or smaller than a lower limit value L1. X1 is increased as the order of the set gain changing condition is higher.

2 Claims, 8 Drawing Sheets

FIG. 6

| | GAIN CHANGING CONDITION | | | | GAIN CHANGING RANGE | |
|---|---|---|---|---|---|---|
| | $X_1$ | $Y_1$ | LOWER LIMIT VALUE $L_1$ | UPPER LIMIT VALUE $U_1$ | DECREASE LIMIT | INCREASE LIMIT |
| MODE M1 | 1 | 1 | 800 | 2,000 | 1/3 TIMES | 3 TIMES |
| MODE M2 | 3 | 2 | 600 | 2,500 | 1/1.8 TIMES | 1.8 TIMES |
| MODE M3 | 10 | 7 | 600 | 2,500 | 1/1.8 TIMES | 1.8 TIMES |

FIG. 7

| | $X_2$, $X_3$ | $Y_2$, $Y_3$ | LOWER LIMIT VALUE $L_2$, $L_3$ | UPPER LIMIT VALUE $U_2$, $U_3$ |
|---|---|---|---|---|
| 1-2 PROGRESS CONDITION | 1 | 1 | 800 | 2,000 |
| 2-3 PROGRESS CONDITION | 3 | 3 | 600 | 2,500 |
| 3-2 REGRESS CONDITION | 10 | 7 | 600 | 2,500 |

PULSE WAVE MEASURING DEVICE

CROSS REFERENCE TO RELATED APPLICATION

The present application is based on Japanese patent application No. 2016-100476 filed on May 19, 2016, the whole contents of which are incorporated herein by reference.

FIELD

The present disclosure relates to a pulse wave measuring device.

BACKGROUND

A conventional pulse wave measuring device uses a pulse wave sensor to acquire a pulse wave signal of a test subject body. The pulse wave measuring device calculates a blood pressure and the like by using the acquired pulse wave signal. A signal level of the pulse wave signal often varies. The pulse wave measuring device therefore controls a gain of the pulse wave sensor as exemplarily disclosed in JP 3584140 (JP H10-234684A).

For controlling the gain, the following method may be adopted. Amplitude of each pulse wave signal is calculated by acquiring plural pulse wave signals for a predetermined time period. A plural number of calculated amplitudes are stored and the gain is controlled based on the stored amplitudes.

In case that a large number of stored amplitudes are required for calculation, a long time period is needed to store a required number of stored amplitudes. As a result, timing to perform the gain control in correspondence to the signal level of the pulse wave signal is delayed. In case that a small number of stored amplitudes are required for calculation, the gain control is likely to be unnecessarily performed in response to external disturbance of a short period.

SUMMARY

It is therefore an object to provide a pulse wave measuring device, which appropriately controls a gain of a pulse wave sensor.

According to one aspect, a pulse wave measuring device comprises a signal acquiring unit, an amplitude storing unit, a gain checking unit, a gain changing unit, a condition storing unit, a mode progress checking unit and a mode progressing unit. The signal acquiring unit acquires a pulse wave signal by way of a pulse wave sensor. The amplitude storing unit stores amplitude of the pulse wave signal acquired by the signal acquiring unit. The gain checking unit checks whether the amplitude stored in the amplitude storing unit satisfies a predetermined gain changing condition. The gain changing unit changes a gain of the pulse wave sensor when the gain checking unit determines that the gain changing condition is satisfied. The condition storing unit stores plural gain changing conditions, which are assigned with sequence numbers. The mode progress checking unit for checking whether the amplitude stored in the amplitude storing unit satisfies a predetermined mode progress condition. The mode progressing unit changes, when the mode progress checking unit determines that the sequence number of the gain changing condition at present time is other than a last number and the mode progress condition is satisfied, the gain changing condition, which the gain checking unit uses, to the gain changing condition, the sequence number of which follows the sequence number of the gain changing condition of the present time.

Assuming that X1, Y1, X2 and Y2 are natural numbers, U1, L1, U2 and L2 are real numbers, which are equal to or larger than 0, X1 is equal to or larger than Y1, and X2 is equal to or larger than Y2, U1 is equal to or larger than L1 and U2 is equal to or larger than L2, the gain changing condition is that Y1 or more pieces of the amplitudes among latest X1 pieces of the amplitudes stored in the amplitude storage unit is larger than an upper limit value U1 or smaller than a lower limit value L1, and X1 increases as the sequence number increases. The mode progress condition is that Y2 or more pieces of the amplitudes among latest X2 pieces of the amplitudes stored in the amplitude storage unit remain same or are corrected by the gain changed by the gain changing unit, and smaller than an upper limit value U2 and larger than a lower limit value L2, and X2 increases as the sequence number set at present time increases.

BRIEF DESCRIPTION OF THE DRAWINGS

FIG. 6 is a data chart showing a gain changing condition and a gain changing range in modes M1 to M3;

FIG. 7 is a data chart showing a M1-M2 progress condition, a M2-M3 progress condition and a M3-M2 regression condition;

DETAILED DESCRIPTION OF THE EMBODIMENT

A pulse wave measuring device will be described below with reference to embodiments shown in the accompanying drawings.

First Embodiment

Figure 1:
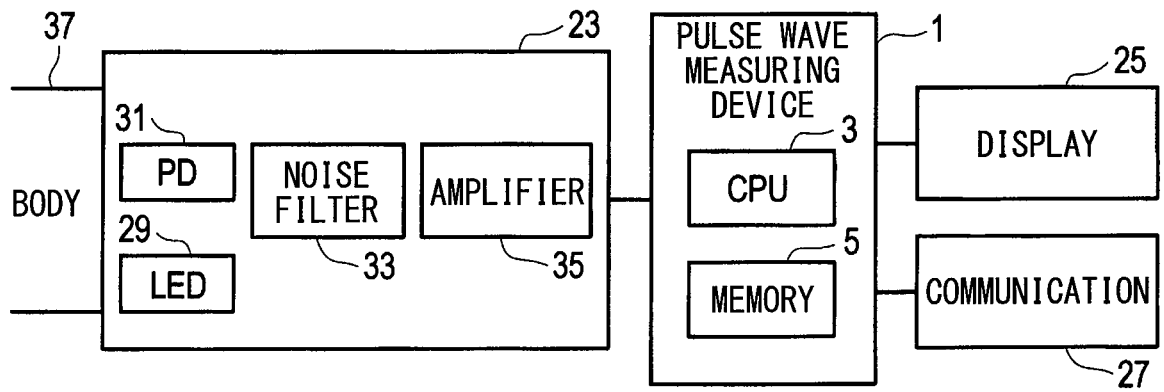
FIG. 1 is a block diagram showing a configuration of a pulse wave measuring device.
Figure 2:
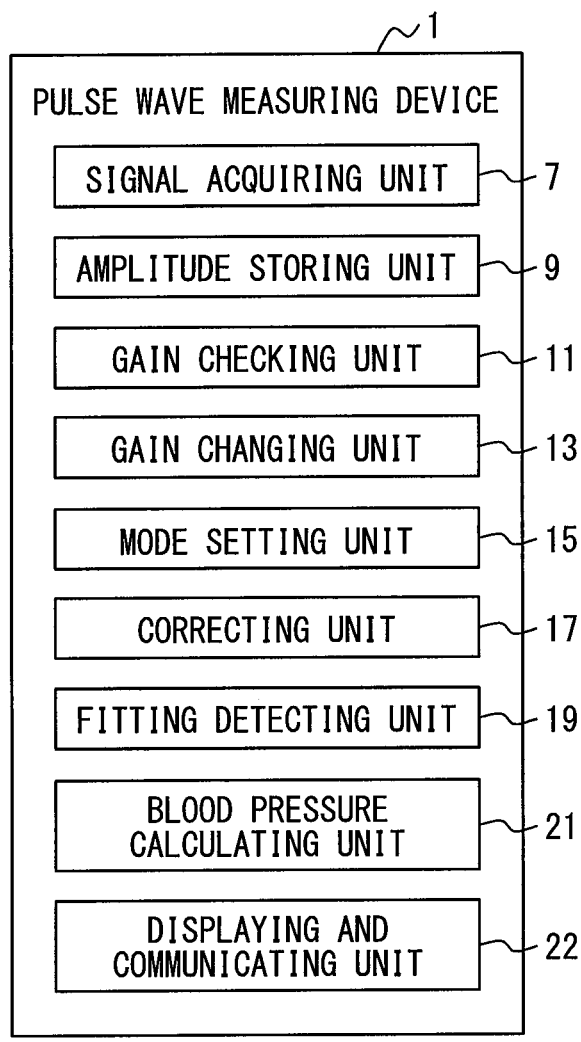
FIG. 2 is a block diagram showing a functional configuration of the pulse wave measuring device.

Referring to FIG. 1 and FIG. 2, a pulse wave measuring device 1 is designated with a reference numeral 1. The pulse wave measuring device 1 is formed of primarily a microcomputer, which includes a CPU 3, a semiconductor memory 5 such as a RAM, a ROM and a flash memory. Each function of the pulse wave measuring device 1 is realized by the CPU 3, which executes programs stored in a non-transitional storage medium. In this example, the memory 5 is the non-transitional storage medium. By execution of the stored programs, functions corresponding to the programs are performed. The pulse wave measuring device 1 may include one or more microcomputers.

As shown in FIG. 2, the pulse wave measuring device 1 includes, as functional structures realized by execution of the programs stored in the memory 5 by the CPU 3, a signal acquiring unit 7, amplitude storing unit 9, a gain checking unit 11, a gain changing unit 13, a mode setting unit 15, a correcting unit 17, a fitting detecting unit 19, a blood pressure calculating unit 21 and a displaying and communicating unit 22. These functional structures forming the pulse wave measuring device 1 need not be realized by only software but may be realized partly or wholly by hardware as a combination of logic circuits, analog circuits and the like. The mode setting unit 15 corresponds to a mode progress checking unit, a mode progressing unit, a mode regression checking unit, a mode regressing unit, a saturation checking unit and a prohibiting unit.

The pulse wave measuring device 1 may be used in combination with a pulse wave sensor 23, a display 25 and a communication device 27.

The pulse wave sensor 23 is worn or fit on a part of a test subject body 37. The part of the body may be a wrist, a finger top and the like. The pulse wave sensor 23 includes a light-emitting diode (LED) 29, a photo diode (PD) 31, a noise filter 33 and an amplifier circuit 35.

The LED 20 irradiates visible light to skin of the test subject body 37. This light has a wavelength of 5,000 Å to 7,000 Å. A part of the light irradiated to the test subject body 37 is reflected in capillary blood vessels of skin.

The PD 31 receives a part of light, which is irradiated by the LED 29 to the skin and reflected in the capillary blood vessels, and outputs an electric signal. This electric signal is a pulse wave signal, which varies with a pulse wave of the test subject body 37.

The noise filter 33 filters out noises in the pulse wave signal. The amplifier circuit 35 amplifies the pulse wave signal, which has been noise-filtered. The pulse wave sensor 23 outputs an amplified pulse wave signal to the pulse wave measuring device 1. A gain of the pulse wave sensor 23 is determined based on a quantity of light of the LED 29 and an amplification factor of the amplifier circuit 35. The gain increases as the light quantity of the LED 29 increases. The gain also increases as the amplification factor of the amplifier circuit 35 increases. The light quantity of the LED 29 and the amplification factor of the amplifier circuit 35 are controlled by the pulse wave measuring device 1. The gain of the pulse wave sensor 23 is thus controlled by the pulse wave measuring device 1.

The display 25 displays an image in correspondence to information outputted from the pulse wave measuring device 1. The communication device 27 transmits the information outputted from the pulse wave measuring device 1 to external devices.

Figure 3:
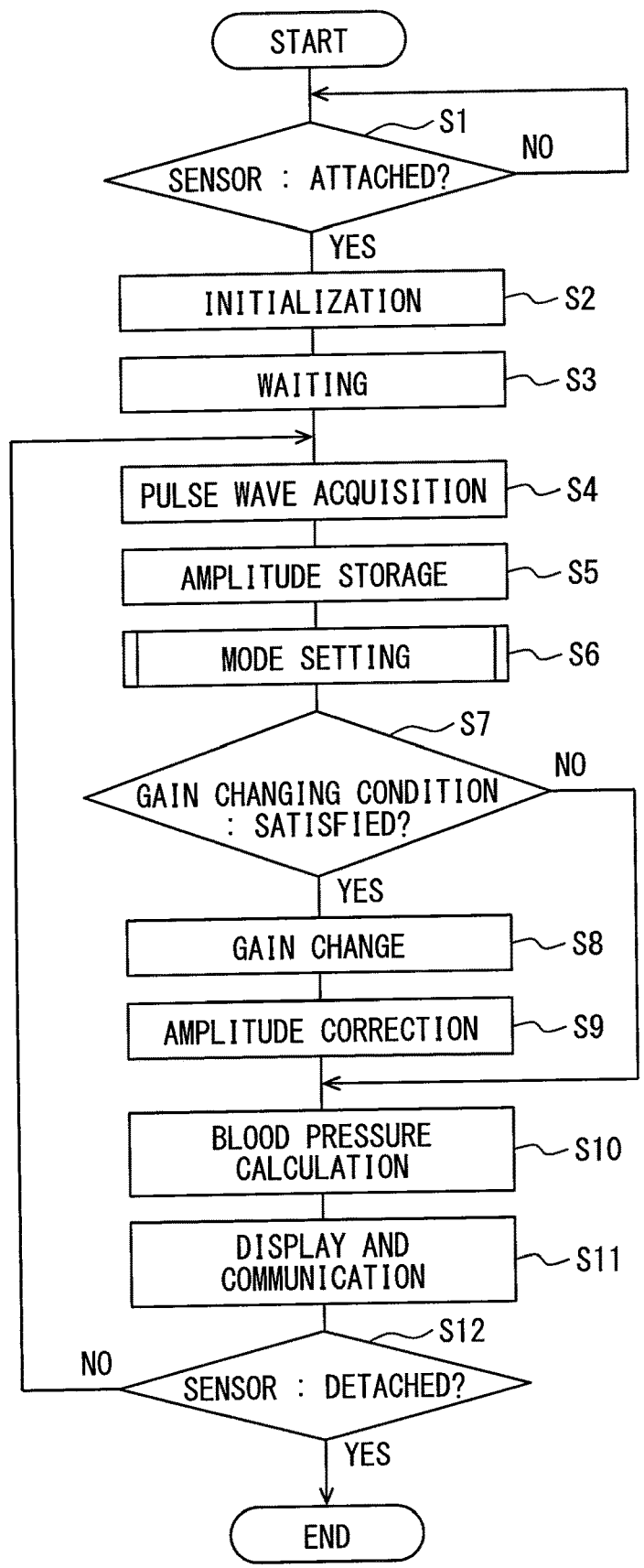
FIG. 3 is a flowchart showing whole processing executed by the pulse wave measuring device.
Figure 4:
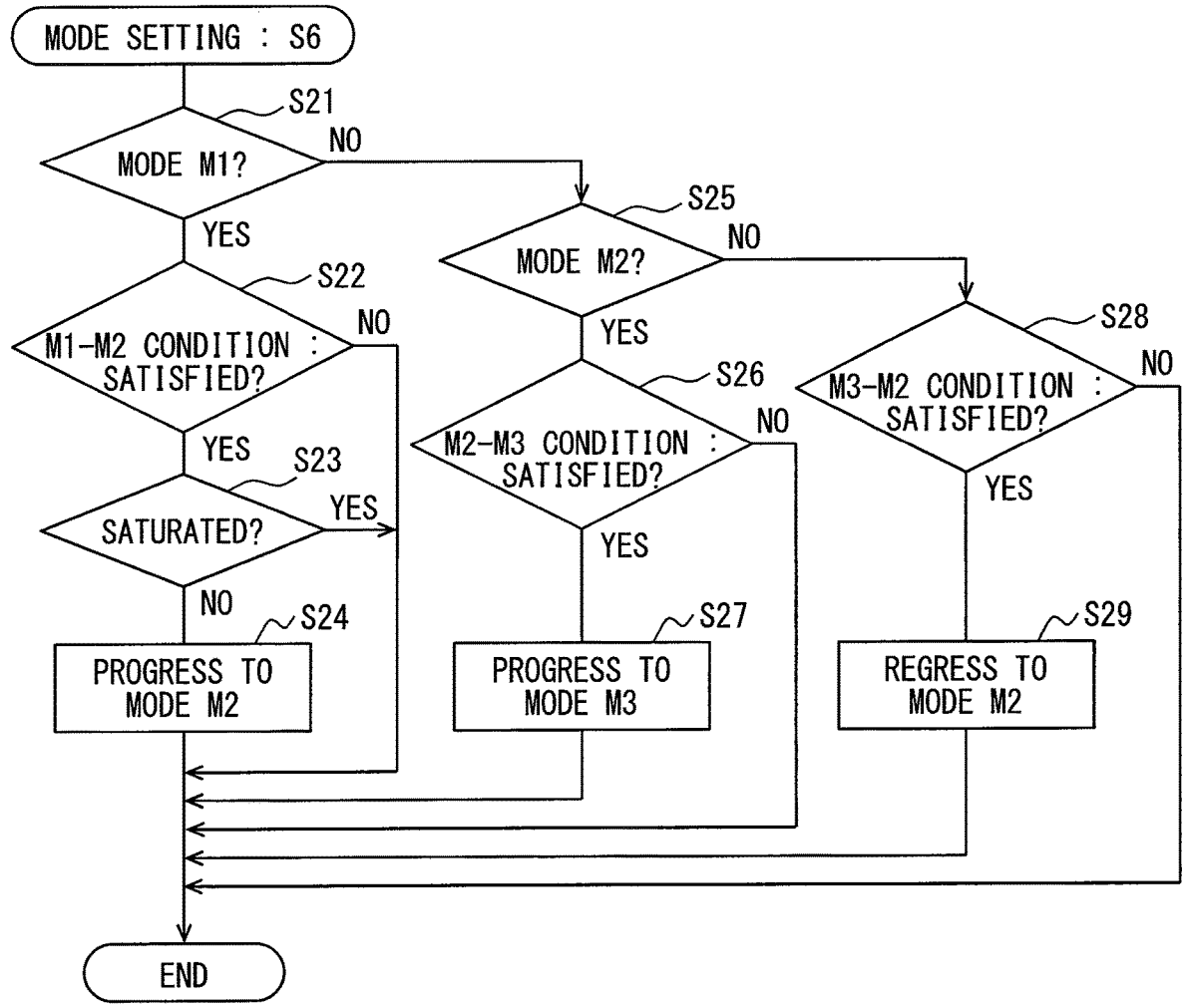
FIG. 4 is a flowchart showing mode setting processing executed by the pulse wave measuring device.

Processing executed by the pulse wave measuring device 1 are shown in FIG. 3 to FIG. 7. The processing shown in FIG. 3 is executed when power supply to the pulse wave measuring device 1 is turned on. At step S1, the fitting detecting unit 19 checks whether the pulse wave sensor 23 is worn by the test subject body 37. The fitting detecting unit 19 checks whether the pulse wave sensor 23 is fit on the test subject body 37 based on a magnitude of a signal level of the pulse wave signal outputted from the pulse wave sensor 23. Upon determination that the pulse wave sensor 23 is worn and not worn by the test subject body 37, the fitting detecting unit 17 executes step S2 and step S1 again, respectively.

At step S2, the mode setting unit 15 executes an initial setting. In the initial setting, the gain of the pulse wave sensor 23 is set to an initial value and a mode is set to mode M1. The initial value of the gain is an average value of gains, which has been used immediately before the power supply to the pulse wave measuring device 1 is turned off in the past. The initial value may alternatively be a fixed value.

The mode defines a gain changing condition and a gain changing range as shown in FIG. 6. The gain changing condition indicates a requirement to be satisfied. When the requirement is satisfied and not satisfied, the gain is changed and not changed, respectively. The gain changing range indicates a range of change, which is permissible at the time of changing a gain. The gain changing condition and the gain changing range will be described later in detail.

The mode includes three types of modes M1 to M3. Each of the modes M1 to M3 defines the gain changing condition and the gain changing range. Numbers 1 to 3 fitted to the mode indicate the order of sequence. The mode M1 is the first mode in the sequence. The modes M2 and M3 are modes, which are not the first in the sequence. The mode M3 is the last mode in the sequence. The modes M1 to 3 are stored in the memory 5. The memory 5 thus corresponds to a condition storing unit.

At step S3 in FIG. 3, a predetermined period of time is waited as a wait period from time of determination at step S1 that the pulse wave sensor 23 is worn. This wait period may be between 0.5 to 1.5 seconds.

Figure 5:
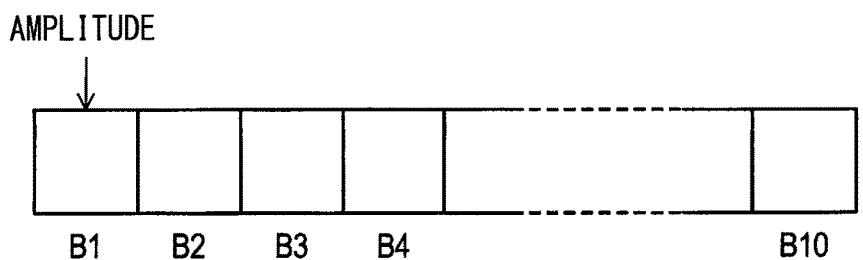
FIG. 5 is an explanatory diagram showing a configuration of buffers.

At step S4, the signal acquiring unit 7 acquires the pulse wave signal by using the pulse wave sensor 23. The pulse wave is acquired for a period of 1.0 s. At step S5, the amplitude storing unit 9 calculates amplitude of the pulse wave signal acquired at step S4 and stores a calculated amplitude. As shown in FIG. 5, ten buffers B1 to B10 are provided in the memory 5. At step S5, the amplitude of the pulse wave signal acquired at the immediately preceding step S4 is stored in the buffer B1. Past amplitudes, which have been stored in the buffers B1 to B9 before, are transferred to the buffers B2 to B10. The amplitude, which has been stored in the buffer B10 before, is deleted.

At step S6, the mode setting unit 15 sets a mode. This processing will be described with reference to FIG. 4. At step S21 in FIG. 4, it is checked first whether the mode M1 is set at present time. In case that the mode M1 is set and not set, step S22 and step S25 are executed, respectively.

At step S22, it is checked whether a condition for progressing from the mode M1 to the mode M2 (hereinafter referred to as M1-M2 progress condition) is satisfied. The M1-M2 progress condition is that (1) the latest one amplitude, which is stored in the buffer B1 and not corrected, is equal to or smaller than 2,000 and equal to or larger than 800 or (2) the latest one amplitude stored in the buffer B1 may be made to be equal to 2,000 or smaller and equal to or larger than 800 by correction. The M1-M2 progress condition corresponds to the mode progress condition.

The correction is to change the gain within the gain changing range in the mode M1 and correct the amplitude with the changed gain. For example, the latest one amplitude stored in the buffer B1 is assumed to be 500. This amplitude is changed to 1,000 by increasing the gain by two times within the gain changing range in the mode M1 and correcting the amplitude with the changed gain. Since 1,000 is smaller than 2,000 and larger than 800, the condition (2) described above is satisfied.

The latest one amplitude, which is used to check whether the M1-M2 progress condition is satisfied, corresponds to X2. Further, the latest one amplitude, which need be equal to or smaller than 2,000 and equal to or larger than 800 to satisfy the M1-M2 progress condition, corresponds to Y2. 2,000 and 800 correspond to an upper limit value U2 and a lower limit value L2.

In case that the M1-M2 progress condition is satisfied, step S23 is executed. In case that the M1-M2 progress condition is not satisfied, the mode setting processing is finished while maintaining the mode M1. At step S23, it is checked whether the pulse wave signal acquired at immediately preceding step S4 saturated in the pulse wave sensor 23. In case that it does not saturate, step S24 is executed. In case that it saturated, the mode setting processing is finished while maintaining the mode M1. Maintaining the mode M1 in case of saturation of the pulse wave signal corresponds to prohibition of a mode change from the mode M1 to the mode M2.

At step S24, the mode set in the pulse wave measuring device 1 is changed from the mode M1 to the mode M2. In case that step S21 results in NO, step S25 is executed. At step S25, it is checked whether the mode M2 is set at present. In case that the mode M2 is set and not set, step S26 and step S28 are executed, respectively.

At step S26, it is checked whether the condition for progressing from the mode M2 to the mode M3 (hereinafter referred to as M2-M3 progress condition) is satisfied. The M2-M3 progress condition is that (1) all of the latest three amplitudes, which are stored in the buffers B1 to B3 and not corrected, are equal to or smaller than 2,500 and equal to or larger than 600 or (2) all of the latest three amplitudes stored in the buffers B1 to B3 may be made to be equal to 2,500 or smaller and equal to or larger than 600 by correction. The M2-M3 progress condition corresponds to the mode progress condition.

The correction is to change the gain within the gain changing range in the mode M2 and correct the amplitude with the changed gain. For example, the latest three amplitudes stored in the buffers B1 to B3 are all assumed to be 500. Each of these three amplitudes is changed to 750 by increasing the gain by one and a half times within the gain changing range in the mode M2 and correcting the amplitude with the changed gain. Since 750 is smaller than 2,500 and larger than 600, the condition (2) described above is satisfied.

The latest three amplitudes, which are used to check whether the M2-M3 progress condition is satisfied, corresponds to X2. Further, the latest three amplitudes, which need be equal to or smaller than 2,500 and equal to or larger than 600 to satisfy the M2-M3 progress condition, corresponds to Y2. 2,500 and 600 correspond to the upper limit value U2 and the lower limit value L2.

In case that the M2-M3 progress condition is satisfied, step S27 is executed. In case that the M2-M3 progress condition is not satisfied, the mode setting processing is finished while maintaining the mode M2. At step S27, the mode set in the pulse wave measuring device 1 is changed from the mode M2 to the mode M3.

In case that step S25 results in NO, step S28 is executed. Step S28 is executed when the mode M3 is set at present. At step S28, it is checked whether the condition for regressing from the mode M3 to the mode M2 (hereinafter referred to as M3-M2 regression condition) is satisfied. The M3-M2 regression condition is that seven or more amplitudes among the latest ten amplitudes, which are stored in the buffers B1 to B10 are larger than 2,500 or smaller than 600. The M3-M2 regression condition corresponds to the mode regression condition.

"10" of the latest ten amplitudes, which are used to check whether the M3-M2 regression condition is satisfied, corresponds to X3. Further, "7" of the latest seven amplitudes, which need be larger than 2,500 or smaller than 600 to satisfy the M3-M2 regression condition, corresponds to Y3. 2,500 and 600 correspond to an upper limit value U3 and a lower limit value L3.

In case that the M3-M2 regression condition is satisfied, step S29 is executed. In case that the M3-M2 regression condition is not satisfied, the mode setting processing is finished while maintaining the mode M3.

After the mode setting step S6 described above, at step S7 in FIG. 3, the gain checking unit 11 checks whether the gain changing condition is satisfied. The gain changing condition used at this step is the gain changing condition, which is defined in the mode set at step S6. The gain changing condition in case that the mode M1 is set at the present time is that the latest one amplitude stored in the buffer B1 is larger than 2,000 or smaller than 800.

"1" of the one amplitude used to check whether the gain changing condition is satisfied corresponds to X1. "1" of the one amplitude, which need be larger than 2,000 or smaller than 800 to satisfy the gain changing condition, corresponds to Y1. 2,000 and 800 correspond to the upper limit value U1 and the lower limit value L1, respectively.

The gain changing condition, which is used in case that the mode M2 is set at the present time, is that two or more amplitudes among the latest three amplitudes stored in the buffers B1 to B3 are larger than 2,500 or smaller than 600.

"3" of the three amplitudes used to check whether the gain changing condition is satisfied corresponds to X1. "2" of the two amplitudes, which need be larger than 2,500 or smaller than 600 to satisfy the gain changing condition, corresponds to Y1. 2,500 and 600 correspond to the upper limit value U1 and the lower limit value L1, respectively.

The gain changing condition, which is used in case that the mode M3 is set at the present time, is that seven or more amplitudes among the latest ten amplitudes stored in the buffers B1 to B10 are larger than 2,500 or smaller than 600.

"10" of the ten amplitudes used to check whether the gain changing condition is satisfied corresponds to X1. "7" of the seven amplitudes, which need be larger than 2,500 or smaller than 600 to satisfy the gain changing condition, corresponds to Y1. 2,500 and 600 correspond to the upper limit value U1 and the lower limit value L1, respectively. X1 and Y1 as well as the lower limit value L1 and the upper limit value U1 in the modes M1 to 3 are shown in FIG. 6. The value X1 increases as the mode progressively changes from the mode M1 to the mode M3.

In case that the gain changing condition is satisfied and not satisfied, step S8 and 10 are executed, respectively. At step S8, the gain changing unit 13 changes the gain. The gain changing unit 13 determines the gain so that as many amplitudes as possible among the latest X1 pieces of amplitudes stored in the buffers B1 to B10 may become larger than the lower limit value L1 and smaller than the upper limit value U1. The gain changing unit 13 thus adjusts the amount of change in correspondence to the latest X1 pieces of the amplitudes stored in the buffers B1 to B10. The number X1, the lower limit value L1 and the upper limit value U1 are defined by the mode, which is set at the present time. However, the change amount of gain is limited to be within the gain changing range, which is determined mode by mode. The gain changing range determined for each mode is shown in FIG. 6.

At step S9, the correcting unit 17 corrects the amplitudes stored in the buffers B1 to B10 in correspondence to the gain changed at step S8. For example, it is assumed that amplitude value 1,000 is stored in the buffer B1 and the gain is doubled at step S9. In this case, the amplitude stored in the buffer B1 is corrected to 2,000. In the processing executed at steps S6 and S7 after this correction, the corrected amplitude is used.

At step S10, the blood pressure calculating unit 21 calculates a blood pressure based on the conventional calculation method by using the pulse wave signal acquired at step S4. At step S11, the displaying and communicating unit 22 displays the blood pressure calculated at step S10 on the display 25. The displaying and communicating unit 21 further transmits the blood pressure calculated at step S10 to the external device by way of the communication device 27.

At step S12, fitting detecting unit 19 checks whether the pulse wave sensor 23 is detached or taken off from the test subject body 37. The fitting detecting unit 19 checks whether the pulse wave sensor 23 is detached from the test subject body 37 based on the magnitude of the signal level of the pulse wave signal outputted from the pulse wave sensor 23. Upon determination that the pulse wave sensor 23 is not detached yet, step S4 is executed again. Upon determination that the pulse wave sensor 23 is detached, the processing is finished.

The pulse wave measuring device 1 provides the following functions and advantages.

(1A) The pulse wave measuring device 1 sets the mode M2 newly, when the M1-M2 progress condition is satisfied under the state of the mode M1. The pulse wave measuring device 1 further sets the mode M3 newly, when the M2-M3 progress condition is satisfied under the state of the mode M2.

X1 in the gain changing condition in the mode M2 is larger than that in the mode M1. X1 in the gain changing condition in the mode M3 is larger than that in the mode M2. Thus it is possible to more appropriately control the gain in the pulse wave sensor 23. This advantage will be described below with reference to the following example.

Figure 8:
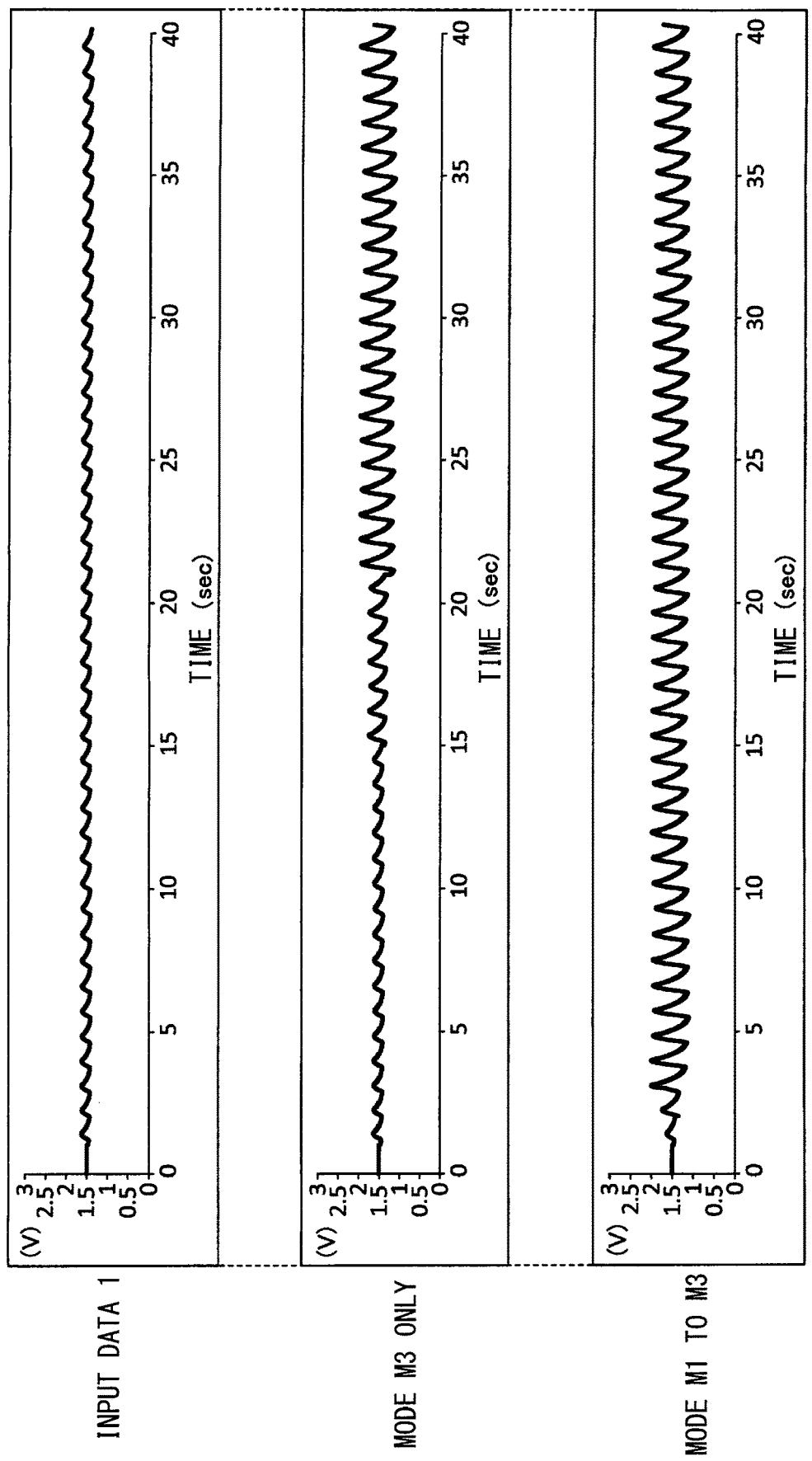
FIG. 8 is an explanatory diagram showing a first input data and pulse waves signal in case that the first input data is gain-controlled.

In FIG. 8, "first input data" shows a first example of a pulse wave signal, amplitude of which increases gradually as time passes. In FIG. 8, "mode M3 only" shows a pulse wave signal in such a case that the first input data is applied to a pulse wave measuring device, which has basically the same configuration as the pulse wave measuring device 1 but is fixed to the mode M3.

In the mode M3, it is checked whether the gain changing condition is satisfied after storing ten amplitudes in the buffers B1 to B10. For this reason, the timing to increase the gain based on the determination that the gain changing condition is satisfied is delayed. As a result, the pulse wave signal having a small amplitude appears for a long period.

In FIG. 8, "modes M1 to M3" shows the pulse wave signal when the first input data is applied to the pulse wave measuring device 1. The pulse wave measuring device 1 initially uses the modes M1 and M2. In the modes M1 and 2, the number of pulses to be checked is small. It is therefore possible to quickly determine that the gain changing condition is satisfied and increase the gain. That is, it is possible to prevent the timing of performing the gain control from being delayed excessively. As a result, the amplitude of the pulse wave signal can be increased at early time.

Figure 9:
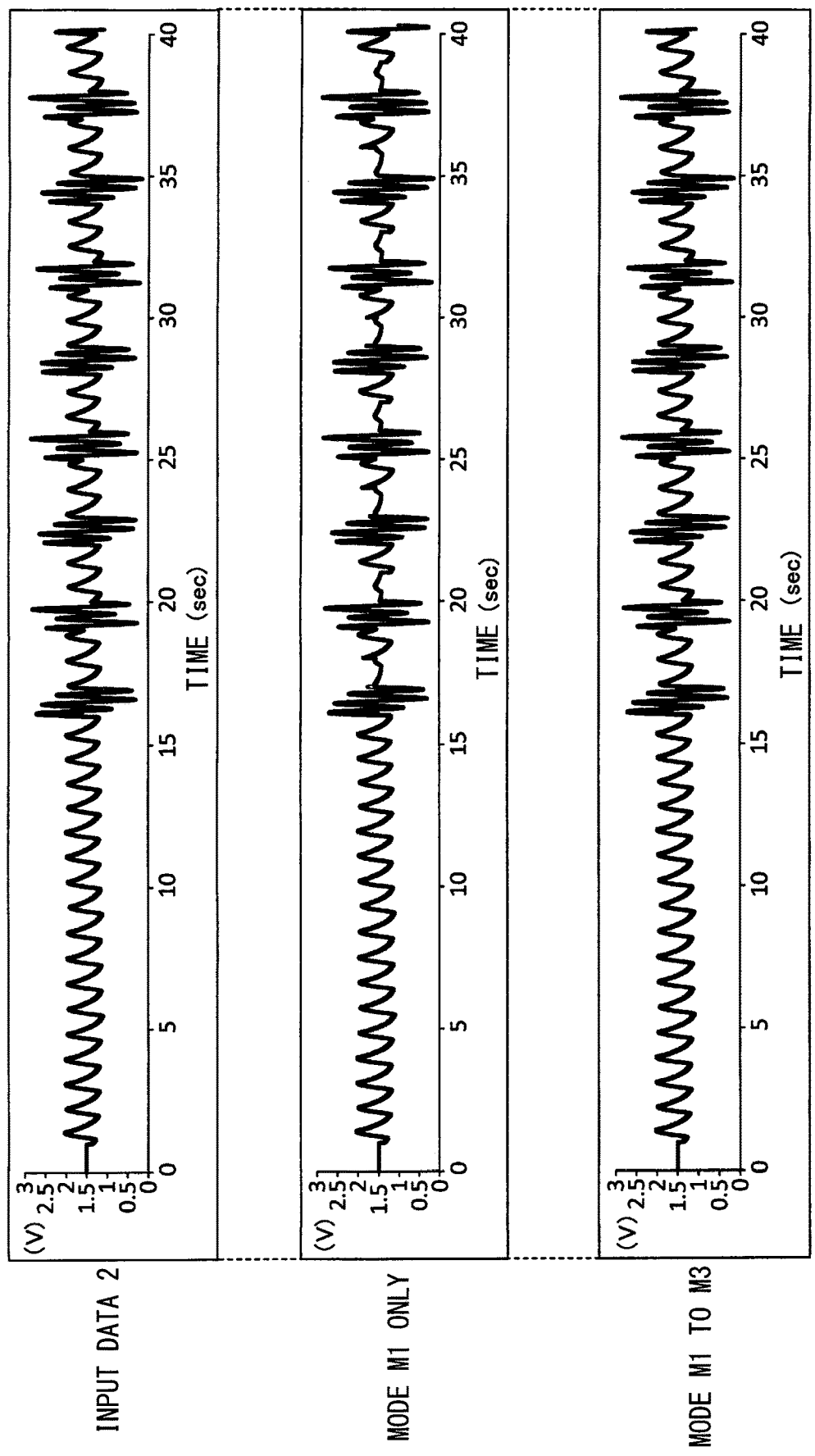
FIG. 9 is an explanatory diagram showing a second input data and pulse wave signals in case that the second input data is gain-controlled.

In FIG. 9, "second input data" shows a second example of a pulse wave signal, on which an external disturbance of short period is superimposed repetitively after 15 seconds from starting of pulse wave signal measurement. In FIG. 9, "mode M1 only" shows a pulse wave signal in such a case that the second input data is applied to the pulse wave measuring device, which has basically the same configuration as the pulse wave measuring device 1 but is fixed to the mode M1.

In the mode M1, it is checked whether the gain should be changed based on only one amplitude. For this reason, the gain is decreased in response to the external disturbance of short period. As a result, the amplitude of the pulse wave signal is decreased excessively in a time period after the external disturbance.

In FIG. 9, "modes M1 to M3" shows the pulse wave signal when the second input data is applied to the pulse wave measuring device 1. The pulse wave measuring device 1 sets the mode M3 when the external disturbance appears. In the mode M3, it is checked whether the gain should be changed based on ten amplitudes. For this reason, it is less likely that the gain is decreased in response to the external disturbance of short period. As a result, it is possible to prevent the gain control from being performed unnecessarily in response to the external disturbance of short period.

With the modes M1 to M3, the pulse wave measuring device 1 is enabled to more appropriately control the gain of the pulse wave sensor 23 than in the case of two modes as described below.

With the modes M1 to M3, the pulse wave measuring device 1 is enabled to more surely maintain the pulse wave signal stably for a long period than in the case of only two modes M1 and M2. This is because the pulse wave measuring device 1 checks in the mode M3 whether the gain should be changed based on that seven or more amplitudes among ten amplitudes are predetermined values.

Further, with the modes M1 to M3, the pulse wave measuring device 1 is enabled to more appropriately control the pulse wave signal under the following exemplary situation than in the case of only modes M1 and M3. The exemplary situation is that, although the pulse wave signal is unstable in the initial period of measurement, the mode progress condition is satisfied accidentally and the mode is changed to the mode, which is one mode ahead of the mode M1. In this situation, in case that three modes M1 to M3 are provided, the mode is not changed to the mode M3 directly but is changed to the mode M2. As a result, it is possible to appropriately control the amplitude of the pulse wave signal in a short period than in case of a direct mode change to the mode M3.

With the modes M1 to M3, the pulse wave measuring device 1 is enabled to more appropriately control the amplitude of the pulse wave signal in the initial period of measurement than in case of only the modes M2 and M3. This is because it is possible to check within a short period whether the gain should be changed based on the value of one amplitude.

(1B) It is more difficult to satisfy the M2-M3 progress condition than not satisfying the gain changing condition in the mode M2. That is, satisfaction of the M2-M3 progress condition does not satisfy the gain changing condition in the mode M2. On the other hand, even in case that the gain changing condition is not satisfied in the mode M2, the M2-M3 progress condition may not be satisfied.

For this reason, it is possible to improve the response characteristic of the gain control and prevent the gain from being controlled excessively.

(1C) The lower limit value L1 in the mode M2 is smaller than the lower limit value L1 in the mode M1. The lower limit value L1 in the mode M3 is the same as the lower limit value L1 in the mode M2. The upper limit value U1 in the mode M2 is smaller than the upper limit value U1 in the mode M1. The upper limit value U1 in the mode M3 is the same as the upper limit value U1 in the mode M2. That is, as the mode progresses from the mode M1, the mode M2 to the mode M3, the upper limit value U1 increases or maintains the same value and the lower limit value L1 decreases or maintains the same value.

By setting the lower limit value L1 and the upper limit value U1 as described above, it is possible to appropriately control the gain in the mode M1 and suppress the gain control in the modes M2 and M3.

(1D) The pulse wave measuring device 1 is enabled to adjust the change amount of the gain within the predetermined range. It is thus possible to more appropriately control the gain. It is also possible to prevent the gain from being changed excessively.

(1E) The pulse wave measuring device 1 sets the mode M2 newly when the M3-M2 regression condition is satisfied under the state that mode M3 is set. It is thus possible to more appropriately control the gain in the pulse wave sensor 23. This advantage will be described with reference to the following example.

Figure 10:
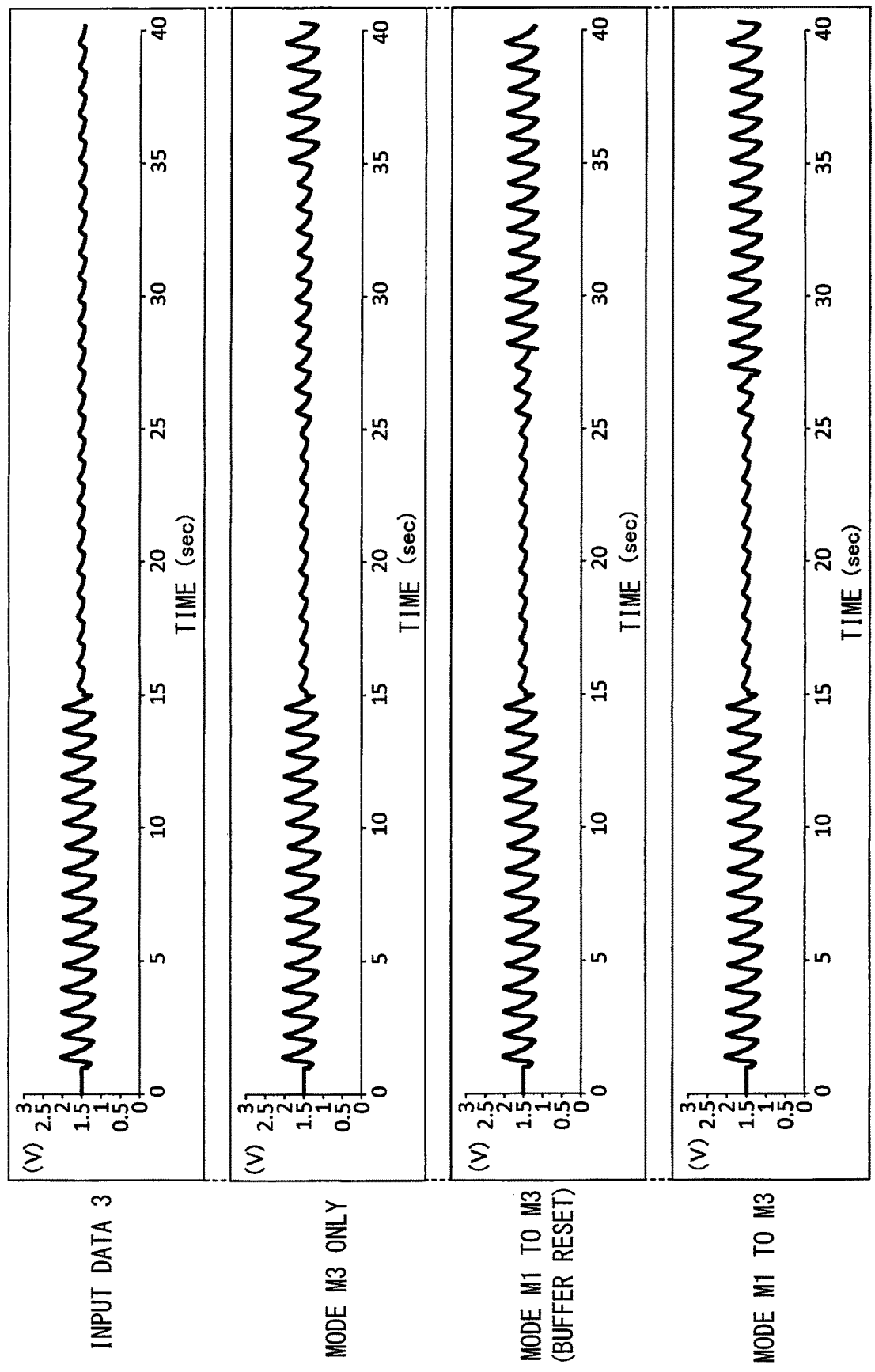
FIG. 10 is an explanatory diagram showing a third input data and pulse wave signals in case that the third input data is gain-controlled.

In FIG. 10, "third input data" shows a third example of a pulse wave signal, which has a decreased amplitude when 15 seconds passes from the start time of measuring the pulse wave signal. In FIG. 10, "mode M3 only" shows a pulse wave signal in such a case that the third input data is applied to the pulse wave measuring device, which has basically the same configuration as the pulse wave measuring device 1 but is fixed to the mode M3.

In the mode M3, it is checked whether the gain changing condition is satisfied after ten amplitudes are stored in the buffers B1 to B10. For this reason, the timing of increasing the gain by determining that the gain changing condition is satisfied is delayed. As a result, it takes a long period to increase the gain after the amplitude starts to decrease in the third input data.

In FIG. 10, "mode M1 to M3" indicates a pulse wave signal in case that the third input data is applied to the pulse wave measuring device 1. At time point that the amplitude decreases in the third input data, the mode M3 is set in the pulse wave measuring device 1. When the amplitude starts to decrease in the third input data, the M3-M2 regression condition is satisfied and the pulse wave measuring device 1 sets the mode M2. In the mode M2, the number of the amplitudes to be checked is small. For this reason, the gain is increased by determining that the gain changing condition is satisfied at early time. As a result, it is possible to increase the amplitude of the pulse wave signal at early time.

(1F) In case that the pulse wave signal saturates, the pulse wave measuring device 1 prohibits a mode change from the mode M1 to the mode M2. It is thus possible to prevent progressing to the mode M2 without satisfaction of the M1-M2 progress condition.

(1G) The pulse wave measuring device 1 corrects the amplitudes stored in the buffers B1 to B10 in correspondence to the gain, which has been changed, in case of the gain change. With this correction, the amplitudes stored before changing of the gain are usable for checking the gain satisfaction condition, M1-M2 progress condition, M2-M3 progress condition and M3-M2 regression condition. As a result, it is possible to perform the gain control and the mode change at earlier time.

(1H) In the mode M1, X1 and Y1 are equal. In the modes M2 and M3, X1 is larger than Y1. For this reason, it is possible to improve the response characteristic of the gain control furthermore.

(1I) In the M1-M2 progress condition, X2 and Y2 are equal. In the M2-M3 progress condition as well, X2 and Y2 are equal. For this reason, it is possible to enhance the reliability for the mode change furthermore.

(1J) The pulse wave measuring device 1 starts acquiring the pulse wave signal after the wait period from detection that the pulse wave sensor 23 is worn by the test subject body. The wait period is in the range of 0.5 to 1.5 seconds. For this reason, it is possible to shorten the period required to acquire a predetermined number of pulse beats stably in the pulse wave signal. Stable acquisition of pulses means acquisition of pulses without changing the gain in the course of acquisition. This advantage will be described with reference to experimental data shown in FIG. 11.

Figure 11:
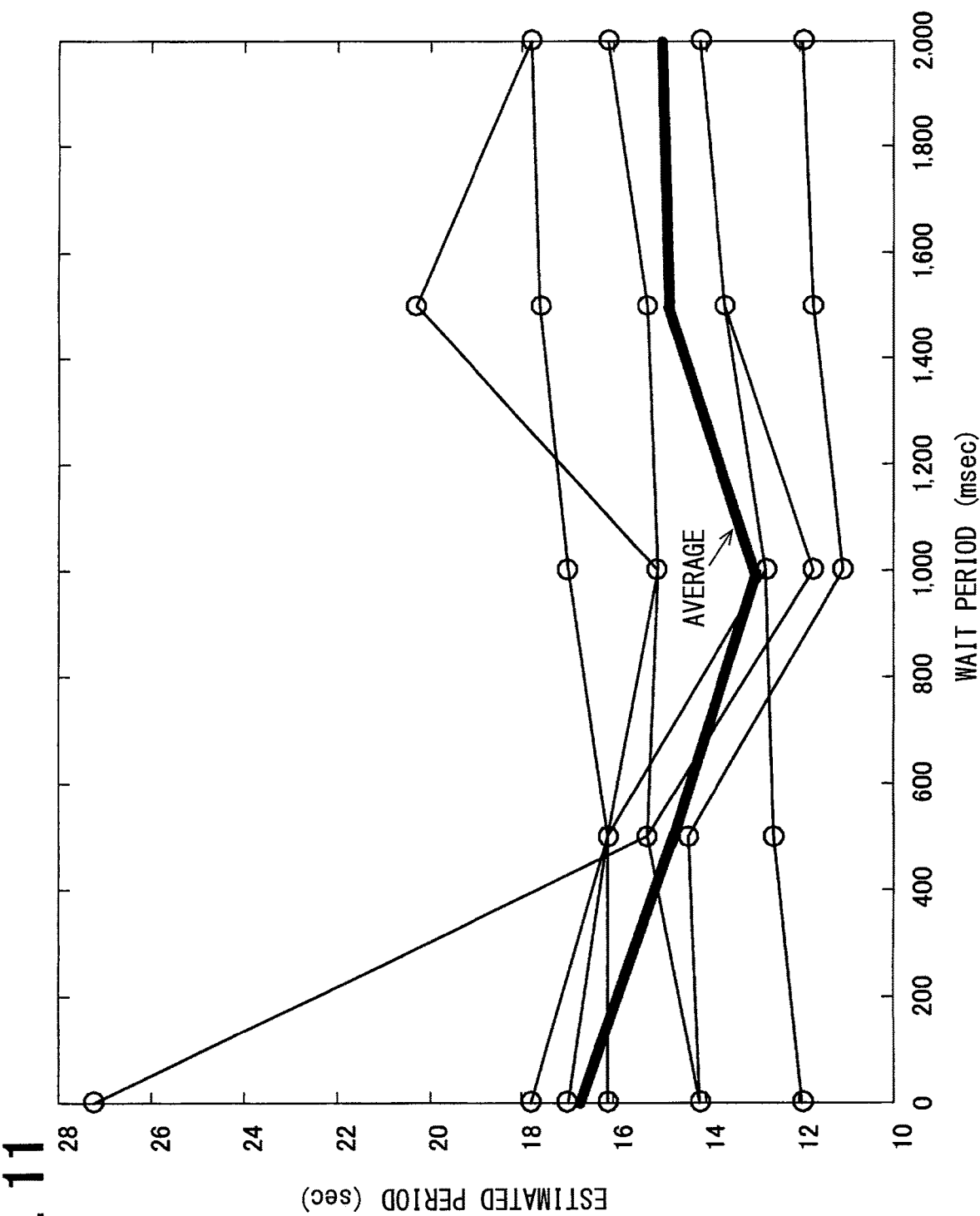
FIG. 11 is a graph showing a relation between and a wait period and an estimated period.

In FIG. 11, the abscissa axis indicates the wait period and the ordinate axis indicates an estimated period, which indicates a period of time required for stably acquiring 10 pulse beats after wearing the pulse wave sensor 23. The estimated periods are measured while carrying the wait period with respect to plural test subject bodies. An average value in FIG. 11 indicates an average value of the estimated periods of plural test subject bodies. As shown in FIG. 11, the estimated periods were shorter in the wait period range between 0.5 to 1.5 seconds (500 to 1,500 milliseconds) than in the other wait periods. The experimental result shown in FIG. 11 proves the advantages described above.

(1K) The pulse wave measuring device 1 is used to calculate the blood pressure by using the pulse wave signal.

Other Embodiment

The pulse wave measuring device 1 described above is not limited to the disclosed embodiment but may be implemented with various modifications as exemplified below.

(1) The pulse wave measuring device 1 may be configured to reset, upon changing the gain, the amplitudes having been stored in the buffers B1 to B10 until the gain change and check the gain changing condition, M1-M2 progress condition, M2-M3 progress condition and M3-M2 regression condition by using the amplitudes stored after the gain change.

In FIG. 10, "modes M1 to M3 (buffer reset)" shows a pulse wave signal in such a case that the third input data is applied to a pulse wave measuring device, which has basically the same configuration as the pulse wave measuring device 1 of the embodiment described above but is a reset-type pulse wave measuring device 1. This reset-type pulse wave measuring device 1 is configured to reset the amplitudes having been stored until the gain change and check the gain changing condition, M1-M2 progress condition, M2-M3 progress condition and M3-M2 regression condition by using the amplitudes stored after the gain change as described above.

The reset-type pulse wave measuring device 1 is capable of increasing the amplitude of the pulse wave signal at earlier time when compared with "mode M3 only."

(2) The pulse wave measuring device 1 may be configured to use a different number of modes other than three, for example, two, four, five or the like.

(3) The pulse wave measuring device 1 may be configured to use a fixed value as a change amount used to change the gain.

(4) The pulse wave measuring device 1 may be configured not to change the mode from the mode M3 to the other mode during a period that the power supply is turned on. The pulse wave measuring device 1 may be configured to change the mode from the mode M3 to the mode M1 in case that a predetermined regression condition is satisfied. The pulse wave measuring device 1 may be configured to change the mode from the mode M2 to the mode M1 in case that a predetermined regression condition is satisfied.

(5) The pulse wave measuring device 1 may be configured to allow a mode change whether the pulse wave signal saturates or not.

(6) The pulse wave measuring device 1 may be configured to have a function of calculating a state value other than blood pressure by using the pulse wave signal. The pulse wave measuring device 1 may be configured to transmit the pulse wave signal to an external device through the communication device 27. The external device may be configured to calculate blood pressure and the like by using the pulse signal transmitted as described above.

(7) The upper limit values U1, U2, U3 and the lower limit values L1, L2, L3 may be determined by multiplication of initial values and coefficient smaller than 1. The amplitude calculated from the pulse wave signal may be stored in the buffers B1 to B10 after correction of multiplication by a coefficient larger than 1.

With this modification, even in case that the amplitude calculated from the pulse wave signal is smaller than a true value, influence of such an error may be reduced.

(8) Checking of whether the pulse wave sensor 23 is worn by the test subject body 37 may be performed by other methods. For example, the pulse wave sensor 23 may be determined to be worn by the test subject body 37 when a touch sensor fitted to the pulse wave sensor 23 is turned on.

What is claimed is:

1. A pulse wave measuring device for use with a pulse wave sensor that outputs a pulse wave signal of a test subject body, the pulse wave measuring device comprising:
    a memory for storing predetermined programs and data for measuring a pulse wave of the test subject body; and
    a processor for executing the predetermined programs to attain functions of
        acquiring the pulse wave signal output from the pulse wave;
        storing amplitudes of the pulse wave signal in the memory;
        checking whether the amplitudes satisfy a gain changing condition at a present time among plural gain changing conditions, the plural gain changing conditions being assigned with corresponding sequence numbers that run in a series and stored in the memory;
    changing a gain of the pulse wave sensor when the gain changing condition at the present time is satisfied;
    checking whether the amplitudes satisfy a predetermined mode progress condition; and
    when the respective sequence number of the gain changing condition at the present time is other than a last number of the series of the sequence numbers and the mode progress condition is satisfied, changing the gain changing condition at the present time to the gain changing condition whose sequence number follows the respective sequence number of the gain changing condition at the present time in the series,
    wherein, given that (a) X1, Y1, X2 and Y2 are natural numbers, (b) U1, L1, U2 and L2 are real numbers that are equal to or larger than 0, (c) X1 is equal to or larger than Y1, (d) X2 is equal to or larger than Y2, (e) U1 is equal to or larger than L1, and (f) U2 is equal to or larger than L2;
    the gain changing condition is that (i) Y1 or more pieces of the amplitudes among latest X1 pieces of the amplitudes stored in the memory are larger than an upper limit value U1 or smaller than a lower limit value L1, and (ii) X1 increases as the sequence number increases, and
    the mode progress condition is that (i) Y2 or more pieces of the amplitudes among latest X2 pieces of the amplitudes stored in the memory remain same or are corrected by the gain changed by the function of changing the gain, (ii) Y2 or more pieces of the amplitudes among latest X2 pieces of the amplitudes are smaller than an upper limit value U2 and larger than a lower limit value L2, and (iii) X2 increases as the sequence number increases.

2. The pulse wave measuring device according to claim 1, wherein the processor further attains functions of:
    checking whether the amplitudes stored in the memory satisfy a predetermined mode regression condition; and
    changing the gain changing condition at a present time to the gain changing condition whose sequence number precedes the sequence number at the present time in the series, when the respective sequence number of the gain changing condition at present time is other than a first number of the series of the sequence numbers and the mode regression condition is satisfied,
    wherein, given that (a) X3 and Y3 are natural numbers, (b) U3 and L3 are real numbers that are equal to or larger than 0, (c) X3 is equal to or larger than Y3, and (d) U3 is equal to or larger than L3, the mode regression condition is that Y3 pieces of amplitudes among latest X3 pieces of amplitudes stored in the memory are larger than an upper limit value U3 or smaller than a lower limit value L3.

* * * * *